(12) United States Patent
Lippman et al.

(10) Patent No.: US 12,270,035 B2
(45) Date of Patent: Apr. 8, 2025

(54) FLORIGEN PATHWAY TOOLKIT

(71) Applicant: Cold Spring Harbor Laboratory, Cold Spring Harbor, NY (US)

(72) Inventors: Zachary Lippman, North Bellmore, NY (US); Sebastian Soyk, Cold Spring Harbor, NY (US); Soon-Ju Park, Cold Spring Harbor, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 132 days.

(21) Appl. No.: 16/092,862

(22) PCT Filed: Apr. 7, 2017

(86) PCT No.: PCT/US2017/026635
§ 371 (c)(1),
(2) Date: Oct. 11, 2018

(87) PCT Pub. No.: WO2017/180474
PCT Pub. Date: Oct. 19, 2017

(65) Prior Publication Data
US 2020/0299705 A1    Sep. 24, 2020

Related U.S. Application Data

(60) Provisional application No. 62/321,178, filed on Apr. 11, 2016.

(51) Int. Cl.
*C12N 15/82* (2006.01)
*C12N 9/22* (2006.01)
*A01H 6/82* (2018.01)

(52) U.S. Cl.
CPC .......... *C12N 15/8213* (2013.01); *C12N 9/22* (2013.01); *C12N 15/827* (2013.01); *A01H 6/825* (2018.05); *C12N 2310/20* (2017.05)

(58) Field of Classification Search
None
See application file for complete search history.

(56) References Cited

U.S. PATENT DOCUMENTS

| | | |
|---|---|---|
| 8,865,970 B2 | 10/2014 | Zamir et al. |
| 9,414,553 B2 | 8/2016 | de Haan et al. |
| 9,732,352 B2 | 8/2017 | Lippman et al. |
| 9,896,696 B2 | 2/2018 | Begemann et al. |
| 11,624,074 B2 | 4/2023 | Park et al. |
| 2010/0212046 A1 | 8/2010 | Heldens |
| 2011/0247093 A1 | 10/2011 | Zamir et al. |
| 2012/0144514 A1 | 6/2012 | de Haan et al. |
| 2014/0143898 A1 | 5/2014 | Lippman et al. |
| 2015/0011393 A1 | 1/2015 | Tsuji et al. |
| 2015/0284732 A1 | 10/2015 | Lippman et al. |
| 2020/0199604 A1 | 6/2020 | Lippman et al. |
| 2022/0411809 A1 | 12/2022 | Lippman et al. |

FOREIGN PATENT DOCUMENTS

| | | | |
|---|---|---|---|
| EP | 2647646 A1 | 10/2013 | |
| WO | WO 2010/041190 A1 | 4/2010 | |
| WO | WO-2014081730 A1 * | 5/2014 | ............... A01H 1/02 |
| WO | WO 2017/180474 A1 | 10/2017 | |
| WO | 2018/213538 A1 | 11/2018 | |
| WO | 2018/213547 A1 | 11/2018 | |

OTHER PUBLICATIONS

Pnueli et al. Plant Cell (2001) vol. 13, pp. 2687-2702. (Year: 2001).*
Soyk S. et al. Nature Genetics (Jan. 2017) vol. 49, No. 1; pp. 1-30; incl. suppl. (Year: 2017).*
Park et al., Nature Genetics 2014: 1-6; Epub: Nov. 2, 2014. (Year: 2014).*
International Search Report and Written Opinion for Application No. PCT/US2017/026635 dated Jul. 11, 2017.
International Preliminary Report on Patentability for Application No. PCT/US2017/026635 dated Oct. 25, 2018.
Jiang et al., Tomato yield heterosis is triggered by a dosage sensitivity of the florigen pathway that fine-tunes shoot architecture. PLoS Genet. 2013;9(12):e1004043. doi: 10.1371/journal.pgen.1004043. Epub Dec. 26, 2013.
Park et al., Optimization of crop productivity in tomato using induced mutations in the florigen pathway. Nat Genet. 2014:1-6. doi: 10.1038/ng.3131. Epub Nov. 2, 2014.
Soyk et al., Variation in the flowering gene Self Pruning 5G promotes day-neutrality and early yield in tomato. Nat Genet. Jan. 2017;49(1):162-168. doi: 10.1038/ng.3733. Epub Dec. 5, 2016.
Teo et al., New insights into the regulation of inflorescence architecture. Trends Plant Sci. Mar. 2014;19(3):158-65. doi: 10.1016/j.tplants.2013.11.001. Epub Dec. 3, 2013.
Abe et al., FD, a bZIP protein mediating signals from the floral pathway integrator FT at the shoot apex. Science. Aug. 12, 2005;309(5737):1052-6.
Ahn et al., A divergent external loop confers antagonistic activity on floral regulators FT and TFL1. EMBO J. Feb. 8, 2006;25(3):605-14. Epub Jan. 19, 2006.
Aoki et al., Large-scale analysis of full-length cDNAs from the tomato (*Solanum lycopersicum*) cultivar Micro-Tom, a reference system for the Solanaceae genomics. BMC Genomics. Mar. 30, 2010;11:210. doi: 10.1186/1471-2164-11-210.
Cao et al., Four Tomato Flowering Locus T-Like Proteins Act Antagonistically to Regulate Floral Initiation. Front Plant Sci. Jan. 11, 2016;6:1213. doi: 10.3389/fpls.2015.01213. eCollection 2015.

(Continued)

*Primary Examiner* — Russell Kallis
(74) *Attorney, Agent, or Firm* — Wolf, Greenfield & Sacks, P.C.

(57) ABSTRACT

Described herein is a florigen pathway toolkit that comprises mutations in genes in the florigen pathway in Solanaceae, such as mutations in genes in the florigen pathway in tomatoes, that are useful to quantitatively modulate or adjust the balance of opposing flowering signals to customize and improve shoot architecture and flowering (flowering time) for tomato breeding, particularly for fresh market tomato breeding.

25 Claims, 3 Drawing Sheets
Specification includes a Sequence Listing.

(56) References Cited

OTHER PUBLICATIONS

Carmel-Goren et al., The SELF-PRUNING gene family in tomato. Plant Mol Biol. Aug. 2003;52(6):1215-22.
Genbank Submission; NIH/NCBI, Accession No. NP_0012345345. Lifschitz et al., Nov. 30, 2014. 1 page.
Krieger et al., The flowering gene Single Flower Truss drives heterosis for yield in tomato. Nat Genet. May 2010;42(5):459-63. doi:10.1038/ng.550. Epub Mar. 28, 2010.
Lee et al., Homologous recombination in plant cells after Agrobacterium-mediated transformation. Plant Cell. May 1990;2(5):415-25.
Lifschitz et al., The tomato FT ortholog triggers systemic signals that regulate growth and flowering and substitute for diverse environmental stimuli. Proc Natl Acad Sci U S A. Apr. 18, 2006;103(16):6398-403. Epub Apr. 10, 2006.
McCormick, Transformation of tomato with *Agrobacterium tumefaciens*. In: Plant Tissue Culture Manual, Fundamentals and Applications. 1991, Lindsey, Ed. vol. B6:1-9.
Molinero-Rosales et al., Single Flower Truss regulates the transition and maintenance of flowering in tomato. Planta. Jan. 2004;218(3):427-34. Epub Sep. 23, 2003.
Pnueli et al., Tomato SP-interacting proteins define a conserved signaling system that regulates shoot architecture and flowering. Plant Cell. Dec. 2001;13(12):2687-702.
Quinet et al., Transition to flowering and morphogenesis of reproductive structures in tomato. International Journal of Plant Developmental Biology. 2007;1:64-74.
Samanta et al., CRISPR/Cas9: an advanced tool for editing plant genomes. Transgenic Res. Oct. 2016;25(5):561-73. doi: 10.1007/s11248-016-9953-5. Epub Mar. 24, 2016.
Taoka et al., 14-3-3 proteins act as intracellular receptors for rice Hd3a florigen. Nature. Jul. 31, 2011;476(7360):332-5. doi: 10.1038/nature10272.
Wigge et al., Integration of spatial and temporal information during floral induction in *Arabidopsis*. Science. Aug. 12, 2005;309(5737):1056-9.
Wigge et al., Supplement: integration of spatial and temporal information during floral induction in *Arabidopsis*. Science. Aug. 12, 2005;309(5737):S1-S8.
Martí et al., Genetic and physiological characterization of tomato cv. Micro-Tom. J Exp Bot. 2006;57(9):2037-47. doi: 10.1093/jxb/erj154. Epub May 10, 2006.
Canadian Office Action for Application No. 2892012 dated Aug. 25, 2022.
European Office Action for Application No. EP13857579.0 dated Jun. 7, 2017.
European Office Action for Application No. EP13857579.0 dated Apr. 6, 2022.
International Search Report and Written Opinion for Application No. PCT/US2020/061613 dated Mar. 23, 2021.
International Preliminary Report on Patentability for Application No. PCT/US2020/061613 dated Jun. 9, 2022.
Stallard. A new tomato ideal for urban gardens and even outer space. Cold Spring Harbor Laboratory. Dec. 23, 2019. Retrieved from the internet: <https://www.cshl.edu/a-new-tomato-ideal-for-urban-gardens-and-even-outer-space> on Feb. 25, 2021. 1-5.
Villagarcia et al. Modification of tomato growth by expression of truncated ERECTA protein from *Arabidopsis thaliana*. J Exp Bot. Nov. 2012;63(18):6493-504. doi: 10.1093/jxb/ers305. Epub Oct. 23, 2012.
[No Author Listed], Genetic Mutation, Definition—Merriam-Webster Dictionary, 3 pages.
U.S. Appl. No. 14/443,357, filed May 15, 2015, Lippman et al.
U.S. Appl. No. 17/779,987, filed May 25, 2022, Lippman et al.
CA 2,892,012, Aug. 25, 2022, Canadian Office Action.
EP 13857579.0, Jun. 7, 2017, European Office Action.
EP 13857579.0, Apr. 6, 2022, European Office Action.
PCT/US2020/061613, Mar. 23, 2021, International Search Report and Written Opinion.
PCT/US2020/061613, Jun. 9, 2022, International Preliminary Report on Patentability.

European Office Action for Application No. EP13857579.0 mailed Sep. 28, 2023.
Canadian Office Action for Application No. 3020699 mailed Apr. 17, 2023.
Extended European Search Report for Application No. EP20893126.1 mailed Dec. 6, 2023.
[No Author Listed], Strains detail: tomatoma. Tomato Mutants Archive. <https://tomatoma.nbrp.jp/strainDetailAction.do?mutantId=TOMJPF00005>. Last accessed Sep. 7, 2022.
Anzalone et al., Search-and-replace genome editing without double-strand breaks or donor DNA. Nature. Dec. 2019;576(7785):149-157. doi: 10.1038/s41586-019-1711-4. Epub Oct. 21, 2019.
Banerjee et al., Up, up and away! The economics of vertical farming. J Agric Stud. 2014; 2(1): 40-60.
Benke et al., Future food-production systems: vertical farming and controlled-environment agriculture. Sustain: Science Pract Pol 2018; 13(1): 13-26.
Boch et al., Xanthomonas AvrBs3 family-type III effectors: discovery and function. Annu Rev Phytopathol. 2010;48:419-36.
Boch, TALEs of genome targeting. Nat Biotechnol. Feb. 2011;29(2):135-6.
Brand et al., Meristem maintenance and compound-leaf patterning utilize common genetic mechanisms in tomato. Planta. Sep. 2007;226(4):941-51. doi: 10.1007/s00425-007-0540-0. Epub May 23, 2007.
Brooks et al., Efficient gene editing in tomato in the first generation using the clustered regularly interspaced short palindromic repeats/CRISPR-associated9 system. Plant Physiol. Nov. 2014;166(3):1292-7. doi: 10.1104/pp.114.247577. Epub Sep. 15, 2014.
Burstein et al., New CRISPR-Cas systems from uncultivated microbes. Nature. Feb. 9, 2017;542(7640):237-241. doi: 10.1038/nature21059. Epub Dec. 22, 2016.
Cermak et al., Efficient design and assembly of custom TALEN and other TAL effector-based constructs for DNA targeting. Nucleic Acids Res. Jul. 2011;39(12):e82. doi: 10.1093/nar/gkr218.Epub Apr. 14, 2011. Erratum in: Nucleic Acids Res. Sep. 1, 2011;39(17):7879.
Christian et al., Targeting DNA double-strand breaks with TAL effector nucleases. Genetics. Oct. 2010;186(2):757-61. doi: 10.1534/genetics.110.120717. Epub Jul. 26, 2010.
Elitzur et al., Co-ordinated regulation of flowering time, plant architecture and growth by FASCICULATE: the pepper orthologue of Self Pruning. J Exp Bot. 2009;60(3):869-80.doi: 10.1093/jxb/ern334. Epub Jan. 27, 2009.
Eshed et al., Revolutions in agriculture chart a course for targeted breeding of old and new crops. Science. Nov. 8, 2019;366(6466):eaax0025. doi: 10.1126/science.aax0025. Epub Sep. 5, 2019.
Feng et al., Multigeneration analysis reveals the inheritance, specificity, and patterns of CRISPR/Cas-induced gene modifications in Arabidopsis. Proc Natl Acad Sci U S A. Mar. 25, 2014;111(12):4632-7. doi: 10.1073/pnas.1400822111. Epub Feb. 18, 2014.
Gabsalilow et al., Site- and strand-specific nicking of DNA by fusion proteins derived from MutH and I-SceI or TALE repeats. Nucleic Acids Res. Apr. 2013;41(7):e83. doi: 10.1093/nar/gkt080. Epub Feb. 13, 2013.
Gaj et al., . ZFN, Talen, and CRISPR/Cas-based methods for genome engineering. Trends Biotechnol. Jul. 2013;31(7):397-405. doi: 10.1016/j.tibtech.2013.04.004. Epub May 9, 2013.
Goodstein et al., Phytozome: a comparative platform for green plant genomics. Nucleic Acids Res. Jan. 2012;40(Database issue):D1178-86. doi: 10.1093/nar/gkr944. Epub Nov. 22, 2011.
Harrington et al., Programmed DNA destruction by miniature CRISPR-Cas14 enzymes. Science. Nov. 16, 2018;362(6416):839-842. doi: 10.1126/science.aav4294. Epub Oct. 18, 2018.
Hsu et al., Development and applications of CRISPR-Cas9 for genome engineering. Cell. Jun. 5, 2014;157(6):1262-1278.
Jiang et al., Demonstration of CRISPR/Cas9/sgRNA-mediated targeted gene modification in Arabidopsis, tobacco, sorghum and rice. Nucleic Acids Res. Nov. 2013;41(20):e188. doi: 10.1093/nar/gkt780. Epub Sep. 2, 2013.
Juillerat et al., Optimized tuning of TALEN specificity using non-conventional RVDs. Sci Rep. Jan. 30, 2015;5:8150.

(56) References Cited

OTHER PUBLICATIONS

Katoh et al., MAFFT multiple sequence alignment software version 7: improvements in performance and usability. Mol Biol Evol. Apr. 2013;30(4):772-80. doi: 10.1093/molbev/mst010. Epub Jan. 16, 2013.

Kim et al., A guide to genome engineering with programmable nucleases. Nat Rev Genet. May 2014;15(5):321-34. doi: 10.1038/nrg3686. Epub Apr. 2, 2014.

Kim et al., Hybrid restriction enzymes: zinc finger fusions to Fok I cleavage domain. Proc Natl Acad Sci U S A. Feb. 6, 1996;93(3):1156-60.

Kimura et al., ERECTA-family genes coordinate stem cell functions between the epidermal and internal layers of the shoot apical meristem. Development. Jan. 8, 2018;145(1):dev156380.

Kleinstiver et al., High-fidelity CRISPR-Cas9 nucleases with no detectable genome-wide off-target effects. Nature. Jan. 28, 2016;529(7587):490-5. doi: 10.1038/nature16526. Epub Jan. 6, 2016.

Kwon et al. Rapid customization of Solanaceae fruit crops for urban agriculture. Nat Biotechnol. Feb. 2020;38(2):182-188. doi: 10.1038/s41587-019-0361-2. Epub Dec. 23, 2019.

Lemmon et al., Rapid improvement of domestication traits in an orphan crop by genome editing. Nat Plants. Oct. 2018;4(10):766-770. doi: 10.1038/s41477-018-0259-x. Epub Oct. 1, 2018.

Makarova et al., An updated evolutionary classification of CRISPR-Cas systems. Nat Rev Microbiol. Nov. 2015;13(11):722-36. doi: 10.1038/nrmicro3569. Epub Sep. 28, 2015.

Mandel et al., The ERECTA receptor kinase regulates Arabidopsis shoot apical meristem size, phyllotaxy and floral meristem identity. Development. Feb. 2014;141(4):830-41.

Martellozzo et al., Urban agriculture: a global analysis of the space constraint to meet urban vegetable demand. Envron Res Lett. 2014; 9: 064025. 8 pages.

Martinez, The correct application of *Physalis pruinose* L. (Solanaceae). Taxon. Feb. 1993; 42: 103-4.

Masle et al., The ERECTA gene regulates plant transpiration efficiency in Arabidopsis. Nature. Aug. 11, 2005;436(7052):866-70.

Menda et al., In silico screening of a saturated mutation library of tomato. Plant J. Jun. 2004;38(5):861-72.

Miller et al., A RESTful API for Access to Phylogenetic Tools via the CIPRES Science Gateway. Evol Bioinform Online. Mar. 16, 2015;11:43-8.

Minjuan et al., Evaluation of the growth, photosynthetic characteristics, antioxidant capacity, biomass yield and quality of tomato using aeroponics, hydroponics and porous tube-vermiculite systems in bio-regenerative life support systems. Life Sci Space Res. 2019; 22:68-75.

Moscou et al., A simple cipher governs DNA recognition by TAL effectors. Science. Dec. 11, 2009;326(5959):1501.

Murovec et al., New variants of CRISPR RNA-guided genome editing enzymes. Plant Biotechnol J. Aug. 2017;15(8):917-926. doi: 10.1111/pbi.12736. Epub May 9, 2017.

Naito et al., CRISPRdirect: software for designing CRISPR/Cas guide RNA with reduced off-target sites. Bioinformatics. Apr. 1, 2015;31(7):1120-3. doi: 10.1093/bioinformatics/btu743. Epub Nov. 20, 2014.

Nguyen et al., IQ-TREE: a fast and effective stochastic algorithm for estimating maximum-likelihood phylogenies. Mol Biol Evol. Jan. 2015;32(1):268-74. doi: 10.1093/molbev/msu300. Epub Nov. 3, 2014.

Park et al., Rate of meristem maturation determines inflorescence architecture in tomato. Proc Natl Acad Sci U S A. Jan. 10, 2012;109(2):639-44. doi: 10.1073/pnas.1114963109. Epub Dec. 27, 2011.

Pearson et al., Sustainable urban agriculture: stocktake and opportunities. Int J Agric Sustain 2010; 8(1-2): 7-19.

Pnueli et al., The Self-Pruning gene of tomato regulates vegetative to reproductive switching of sympodial meristems and is the ortholog of CEN and TFL1. Development. Jun. 1998;125(11):1979-89.

Porter et al., A Practical Guide to Genome Editing Using Targeted Nuclease Technologies. Compr Physiol. Mar. 14, 2019;9(2):665-714.

Ramirez et al., Engineered zinc finger nickases induce homology-directed repair with reduced mutagenic effects. Nucleic Acids Res. Jul. 2012;40(12):5560-8. doi: 10.1093/nar/gks179. Epub Feb. 28, 2012.

Ran et al., Genome engineering using the CRISPR-Cas9 system. Nat Protoc. Nov. 2013;8(11):2281-2308. doi: 10.1038/nprot.2013.143. Epub Oct. 24, 2013.

Rees et al., Base editing: precision chemistry on the genome and transcriptome of living cells. Nat Rev Genet. Dec. 2018;19(12):770-788.

Riethoven, Regulatory regions in DNA: promoters, enhancers, silencers, and insulators. Methods Mol Biol. 2010;674:33-42.

Rodriguez-Leal et al., Engineering Quantitative Trait Variation for Crop Improvement by Genome Editing. Cell. Oct. 5, 2017;171(2):470-480.e8. doi: 10.1016/j.cell.2017.08.030. Epub Sep. 14, 2017.

Rodriguez-Leal et al., Evolution of buffering in a genetic circuit controlling plant stem cell proliferation. Nat Genet. May 2019;51(5):786-792. doi: 10.1038/s41588-019-0389-8. Epub Apr. 15, 2019.

Saito et al., Tomatoma: a novel tomato mutant database distributing Micro-Tom mutant collections. Plant Cell Physiol. Feb. 2011;52(2):283-96. doi: 10.1093/pcp/pcr004. Epub Jan. 21, 2011.

Sander, CRISPR-Cas systems for editing, regulating and targeting genomes. Nat Biotechnol. Apr. 2014;32(4):347-55. doi: 10.1038/nbt.2842. Epub Mar. 2, 2014.

Shi et al., Discovery of cancer drug targets by CRISPR-Cas9 screening of protein domains. Nat Biotechnol. Jun. 2015;33(6):661-7. doi: 10.1038/nbt.3235. Epub May 11, 2015.

Shmakov et al., Discovery and Functional Characterization of Diverse Class 2 CRISPR-Cas Systems. Mol Cell. Nov. 5, 2015;60(3):385-97.

Shmakov et al., Diversity and evolution of class 2 CRISPR-Cas systems. Nat Rev Microbiol. Mar. 2017;15(3):169-182.

Shpak, Diverse roles of ERECTA family genes in plant development. J Integr Plant Biol. Dec. 2013;55(12):1238-50. doi: 10.1111/jipb.12108. Epub Oct. 30, 2013.

Silva et al., Meganucleases and other tools for targeted genome engineering: perspectives and challenges for gene therapy. Curr Gene Ther. Feb. 2011;11(1):11-27.

Slaymaker et al., Rationally engineered Cas9 nucleases with improved specificity. Science. Jan. 1, 2016;351(6268):84-8. doi: 10.1126/science.aad5227. Epub Dec. 1, 2015.

Soyk et al., Duplication of a domestication locus neutralized a cryptic variant that caused a breeding barrier in tomato. Nat Plants. May 2019;5(5):471-479. doi: 10.1038/s41477-019-0422-z. Epub May 6, 2019. Erratum in: Nat Plants. Aug. 2019;5(8):903.

Swartwood et al., Development of plant regeneration and *Agrobacterium tumefaciens*-mediated transformation methodology for *Physalis pruinosa*. PCTOC. 2019; 137:465-72.

Taylor et al., Lahedes: the LAGLIDADG homing endonuclease database and engineering server. Nucleic Acids Res. Jul. 2012;40(Web Server issue):W110-6. doi: 10.1093/nar/gks365. Epub May 8, 2012.

Tomlinson et al., Using CRISPR/Cas9 genome editing in tomato to create a gibberellin-responsive dominant dwarf DELLA allele. Plant Biotechnol J. Jan. 2019; 17(1):132-140. doi: 10.1111/pbi.12952. Epub Jun. 22, 2018.

Torii et al., The Arabidopsis ERECTA gene encodes a putative receptor protein kinase with extracellular leucine-rich repeats. Plant Cell. Apr. 1996;8(4):735-46.

Touliatos et al., Vertical farming increases lettuce yield per unit area compared to conventional horizontal hydroponics. Food Energy Secur. Aug. 2016;5(3):184-191.

Tzfira et al., Genome modifications in plant cells by custom-made restriction enzymes. Plant Biotechnol J. May 2012;10(4):373-89. doi: 10.1111/j.1467-7652.2011.00672.x. Epub Jan. 3, 2012.

Van Eck et al., Agrobacterium tumefaciens-Mediated Transformation of Tomato. Methods Mol Biol. 2019; 1864:225-234.

Varkonyi-Gasic et al., Mutagenesis of kiwifruit Centroradialis-like genes transforms a climbing woody perennial with long juvenility and axillary flowering into a compact plant with rapid terminal

(56) References Cited

OTHER PUBLICATIONS flowering. Plant Biotechnol J. May 2019; 17(5):869-880. doi: 10.1111/pbi.13021. Epub Oct. 25, 2018.

Wang et al., Comparison of cytosine base editors and development of the BEable-GPS database for targeting pathogenic SNVs. Genome Biol. Oct. 23, 2019;20(1):218.

Wen et al., CsTFL1 inhibits determinate growth and terminal flower formation through interaction with CsNOT2a in cucumber. Development. Jul. 29, 2019;146(14):dev180166.

Werner et al., Fast track assembly of multigene constructs using Golden Gate cloning and the MoClo system. Bioeng Bugs. Jan. 1, 2012;3(1):38-43. doi: 10.4161/bbug.3.1.18223. Epub Jan. 1, 2012.

Wheeler, Agriculture for space: people and places paving the way. Open Agric. 2017; 2: 14-32.

Xu et al., A cascade of arabinosyltransferases controls shoot meristem size in tomato. Nat Genet. Jul. 2015;47(7):784-92. doi: 10.1038/ng.3309. Epub May 25, 2015.

Yan et al., Functionally diverse type V CRISPR-Cas systems. Science. Jan. 4, 2019;363(6422):88-91. doi: 10.1126/science.aav7271. Epub Dec. 6, 2018.

Zetsche et al., Cpf1 is a single RNA-guided endonuclease of a class 2 CRISPR-Cas system. Cell. Oct. 22, 2015;163(3):759-71. doi: 10.1016/j.cell.2015.09.038. Epub Sep. 25, 2015.

Zhang et al., Phylogenetic and CRISPR/Cas9 Studies in Deciphering the Evolutionary Trajectory and Phenotypic Impacts of Rice ERECTA Genes. Front Plant Sci. Apr. 10, 2018;9:473.

Zhang et al., The emerging and uncultivated potential of CRISPR technology in plant science. Nat Plants. Aug. 2019;5(8):778-794. doi: 10.1038/s41477-019-0461-5. Epub Jul. 15, 2019.

Zhou et al., Large chromosomal deletions and heritable small genetic changes induced by CRISPR/Cas9 in rice. Nucleic Acids Res. 2014;42(17):10903-14. doi: 10.1093/nar/gku806. Epub Sep. 8, 2014.

Kobayashi et al., Genome-wide analysis of intraspecific DNA polymorphism in 'Micro-Tom', a model cultivar of tomato (*Solanum lycopersicum*). Plant Cell Physiol. Feb. 2014;55(2):445-54. doi: 10.1093/pcp/pct181. Epub Dec. 5, 2013.

\* cited by examiner

SEQUENCE LISTING

```
<160> NUMBER OF SEQ ID NOS: 16

<210> SEQ ID NO 1
<211> LENGTH: 116
<212> TYPE: DNA
<213> ORGANISM: Solanum lycopersicum

<400> SEQUENCE: 1
atgcctagag atcctttaat agtttctgga gttgttggag atgttgttga tccattcaca      60
agatgtgtag actttggtgt ggtttacaac aatagggtgg tctataatgg atgttc        116

<210> SEQ ID NO 2
<211> LENGTH: 28
<212> TYPE: DNA
<213> ORGANISM: Solanum lycopersicum

<400> SEQUENCE: 2
atgcctagag atcctttaat ggatgttc                                         28

<210> SEQ ID NO 3
<211> LENGTH: 106
<212> TYPE: DNA
<213> ORGANISM: Solanum lycopersicum
```

<400> SEQUENCE: 3

```
atgcctagag atcctttaat agtttctgga gttgttggag atgttgttga tccattcaca      60
agatgtgtag actttggtgt ggtttacaac aatataatgg atgttc                   106
```

<210> SEQ ID NO 4
<211> LENGTH: 104
<212> TYPE: DNA
<213> ORGANISM: Solanum lycopersicum

<400> SEQUENCE: 4

```
atgcctagag atcttctgga gttgttggag atgttgttga tccattcaca agatgtgtag      60
actttggtgt ggtttacaac aatagggtgg tctaatggat gttc                     104
```

<210> SEQ ID NO 5
<211> LENGTH: 61
<212> TYPE: DNA
<213> ORGANISM: Solanum lycopersicum

<400> SEQUENCE: 5

```
cctagagatc ctttaatagt ttctggagtt ggtttacaac aatagggtgg tctataatgg      60
a                                                                     61
```

<210> SEQ ID NO 6
<211> LENGTH: 20
<212> TYPE: DNA
<213> ORGANISM: Solanum lycopersicum

<400> SEQUENCE: 6

```
cctagagatc ctttaatgga                                                  20
```

<210> SEQ ID NO 7
<211> LENGTH: 51
<212> TYPE: DNA
<213> ORGANISM: Solanum lycopersicum

<400> SEQUENCE: 7

```
cctagagatc ctttaatagt ttctggagtt ggtttacaac aatataatgg a               51
```

<210> SEQ ID NO 8
<211> LENGTH: 528
<212> TYPE: DNA
<213> ORGANISM: Solanum lycopersicum

<400> SEQUENCE: 8

```
atggcttcca aaatgtgtga acccttgtg attggtagag tgattggtga agttgttgat      60
tatttctgtc caagtgttaa gatgtctgtt gtttataaca acaacaaaca tgtctataat     120
ggacatgaat tctttccttc ctcagtaact tctaaaccta gggttgaagt tcatggtggt     180
gatctcagat ccttcttcac actgatcatg atagatccag atgttcctgg tcctagtgat     240
ccatatctca gggaacatct acactggatt gtcacagaca ttccaggcac tacagattgc     300
tcttttggaa gagaagtggt tgggtatgaa atgccaaggc caaatattgg aatccacagg     360
tttgtatttt tgctgtttaa gcagaagaaa aggcaaacaa tatcgagtgc accagtgtcc     420
agagatcaat ttagtagtag aaaattttca gaagaaaatg aacttggctc accagttgct     480 gctgtttct tcaattgtca gagggaaact gccgctagaa ggcgttga                   528
```

<210> SEQ ID NO 9

<211> LENGTH: 654
<212> TYPE: DNA
<213> ORGANISM: Solanum lycopersicum

<400> SEQUENCE: 9

| | |
|---|---|
| atgtggtcat caagcagtga taacagggga ctctctgctt cttcttcttc atcttcatcc | 60 |
| tcatctcatt caccattttc tccaagactc aaaacaatgg aagaagtgtg gaaagatatt | 120 |
| aatctttctt cacttcaaga tcacactacg aattactcta gagatcatca tcatcttcat | 180 |
| gatcataatc atcaagctgc taattttggt ggaatgattt tacaagattt tttggcaagg | 240 |
| ccttttgcta atgaatcttc accagcagca gcagcagcag cagcctcccc tgtttcagct | 300 |
| acaactatgc tgaatttgaa ctctgttcct gagcttcatt tctttgataa cccattgagg | 360 |
| caaaactcaa tcttgcacca accaaatgca agtggaagaa aaagggttgt ccctgaaaca | 420 |
| gaagacaatt ctacagggga tagaagaaat cagaggatga tcaagaacag agagtctgct | 480 |
| gctagatcaa gagctagaaa gcaggcttat atgaacgagt tggaatcaga agtggcacat | 540 |
| ttagttgaag aaaatgcaag gctcaagaag cagcagcaac agttacgagt agatgcagct | 600 |
| aatcaagttc ccaaaaagaa cactctttat cggacgtcaa ctgctccatt ttga | 654 |

<210> SEQ ID NO 10
<211> LENGTH: 654
<212> TYPE: DNA
<213> ORGANISM: Solanum lycopersicum

<400> SEQUENCE: 10

| | |
|---|---|
| atgtggtcat caagcagtga taacagggga ctctctgctt cttcttcttc atcttcatcc | 60 |
| tcatctcatt caccattttc tccaagactc aaaacaatgg aagaagtgtg gaaagatatt | 120 |
| aatctttctt cacttcaaga tcacactacg aattactcta gagatcatca tcatcttcat | 180 |
| gatcataatc atcaagctgc taattttggt ggaatgattt tacaagattt tttggcaagg | 240 |
| ccttttgcta atgaatcttc accagcagca gcagcagcag cagcctcccc tgtttcagct | 300 |
| acaactatgc tgaatttgaa ctctgttcct gagcttcatt tctttgataa cccattgagg | 360 |
| caaaactcaa tcttgcacca accaaatgca agtggaagaa aaagggttgt ccctgaaaca | 420 |
| gaagacaatt ctacagggga tagaagaaat cagaggatga tcaagaacag agagtctgct | 480 |
| gctagatcaa gagctagaaa gcaggcttat atgaacgagt tggaatcaga agtggcacat | 540 |
| ttagttgaag aaaatgcaag gctcaagaag cagcagcaac agttacgagt agatgcagct | 600 |
| aatcaagttc ccaaaaagaa cactctttat cggacgtcaa ctgctctatt ttga | 654 |

<210> SEQ ID NO 11
<211> LENGTH: 654
<212> TYPE: DNA
<213> ORGANISM: Solanum lycopersicum

<400> SEQUENCE: 11

| | |
|---|---|
| atgtggtcat caagcagtga taacagggga ctctctgctt cttcttcttc atcttcatcc | 60 |
| tcatctcatt caccattttc tccaagactc aaaacaatgg aagaagtgtg gaaagatatt | 120 |
| aatctttctt cacttcaaga tcacactacg aattactcta gagatcatca tcatcttcat | 180 |
| gatcataatc atcaagctgc taattttggt ggaatgattt tacaagattt tttggcaagg | 240 |
| ccttttgcta atgaatcttc accagcagca gcagcagcag cagcctcccc tgtttcagct | 300 |
| acaactatgc tgaatttgaa ctctgttcct gagcttcatt tctttgataa cccattgagg | 360 |
| caaaactcaa tcttgcacca accaaatgca agtggaagaa aaagggttgt ccctgaaaca | 420 |

```
gaagacaatt ctacagggga tagaagaaat cagaggatga tcaagaacag agagtctgct      480
gctagatcaa gagctagaaa gcaggcttat atgaacgagt tggaatcaga agtggcacat      540
ttagttgaag aaaatgcaag gctcaagaag cagcagcaac agttacgagt agatgcagct      600
aatcaagttc ccaaaaagaa cactctttat cggacgtcaa ttgctccatt ttga            654

<210> SEQ ID NO 12
<211> LENGTH: 534
<212> TYPE: DNA
<213> ORGANISM: Solanum lycopersicum

<400> SEQUENCE: 12
atgcctagag aacgtgatcc tcttgttgtt ggtcgtgtgg taggggatgt attggaccct       60
ttcacaagaa ctattggcct aagagttata tatagagata gagaagttaa taatggatgc      120
gagcttaggc cttcccaagt tattaaccag ccaaggggttg aagttggagg agatgaccta     180 cgtaccttttt tcactttggt tatggtggac cctgatgctc aagtccgag tgatccaaat     240 ctgagagaat accttcactg gttggtcacc gatattccag ctaccacagg ttcaagttttt    300 gggcaagaaa tagtgagcta tgaaagtcca agaccatcaa tgggaataca tcgatttgta     360
tttgtattat tcagacaatt aggtcggcaa acagtgtatg ctccaggatg gcgtcagaat     420
ttcaacacaa gagattttgc agaactttat aatcttggtt tacctgttgc tgctgtctat     480
tttaattgtc aaagagagag tggcagtggt ggacgtagaa gatctgctga ttga           534

<210> SEQ ID NO 13
<211> LENGTH: 534
<212> TYPE: DNA
<213> ORGANISM: Solanum lycopersicum

<400> SEQUENCE: 13
atgcctagag aacgtgatcc tcttgttgtt ggtcgtgtgg taggggatgt attggaccct       60
ttcacaagaa ctattggcct aagagttata tatagagata gagaagttaa taatggatgc      120
gagcttaggc cttcccaagt tattaaccag ccaaggggttg aagttggagg agatgaccta     180 cgtaccttttt tcactttggt tatggtggac cctgatgctc aagtccgag tgatccaaat     240 ctgagagaat accttcactg gttggtcacc gatattccag ctaccacagg ttcaagttttt    300 gggcaagaaa tagtgagcta tgaaagtcca agaccatcaa tgggaataca tcgatttgta     360
tttgtattat tcagacaatt aggtcggcaa acaatgtatg ctccaggatg gcgtcagaat     420
ttcaacacaa gagattttgc agaactttat aatcttggtt tacctgttgc tgctgtctat     480
tttaattgtc aaagagagag tggcagtggt ggacgtagaa gatctgctga ttga           534

<210> SEQ ID NO 14
<211> LENGTH: 528
<212> TYPE: DNA
<213> ORGANISM: Solanum lycopersicum

<400> SEQUENCE: 14
atggcttcca aaatgtgtga accccttgtg attggtagag tgattggtga agttgttgat       60
tatttctgtc caagtgttaa gatgtctgtt gtttataaca caacaaaca tgtctataat      120 ggacatgaat tctttccttc ctcagtaact tctaaaccta gggttgaagt tcatggtggt      180
gatctcagat ccttcttcac actgatcatg atagatccag atgttcttgg tcctagtgat    240
ccatatctca gggaacatct acactggatt gtcacagaca ttccaggcac tacagattgc     300
```

```
tcttttggaa gagaagtggt tgggtatgaa atgccaaggc caaatattgg aatccacagg    360
tttgtatttt tgctgtttaa gcagaagaaa aggcaaacaa tatcgagtgc accagtgtcc    420
agagatcaat ttagtagtag aaaatttca gaagaaaatg aacttggctc accagttgct    480
gctgttttct tcaattgtca gagggaaact gccgctagaa ggcgttga                 528
```

<210> SEQ ID NO 15
<211> LENGTH: 839
<212> TYPE: DNA
<213> ORGANISM: Solanum lycopersicum

<400> SEQUENCE: 15

```
ccatctcatg taataaacaa aaattgagct tattaattat aattgagaag aaaaaaaatc     60
atgcctagag atcctttaat agtttctgga gttgttggag atgttgttga tccattcaca    120
agatgtgtag actttggtgt ggtttacaac aatagggtgg tctataatgg atgttccttg    180
aggccttcac aagttgtcaa tcaacctagg gttgacattg atggagacga tcttcgtact    240
ttttacactc tgattatggt ggatcctgat gctccaaacc ctagcaaccc aaacctgagg    300
gaatatttgc actggttggt cacagatatc ccagcagcca caggagcaac ctttggcaat    360
gaagtcgtgg gctacgagag cccacgaccc tcaatgggaa tccatcgtta tattttcgtg    420
ttgtatcgac aattgggctg cgatgccatc gatgcaccgg acataatcga ttctagacaa    480
aatttcaaca aagagactt tgctaggttt cacaatctag gtttgcctgt tgctgctgtt    540
tacttcaatt gcaatagga aggtggtacc ggtggtcgtc gcctataaat cacccccctc    600
tcctcggggt gcgatccgtt ctcgaactct gtgtcaatgt cagatgtttt gtgtaacgga    660
ttttttgttt gatagtcact cagctaaatt gcttattaac tcagaaagtc attttctttt    720
ttatcgaaga aaattgaaat tatgagataa tagctattat agttgagtga taatctgaaa    780 aaaaaatca accataatat atattatata ttatatatat acccaaaaaa taaaagtct    839
```

<210> SEQ ID NO 16
<211> LENGTH: 187
<212> TYPE: PRT
<213> ORGANISM: Homo sapiens

<400> SEQUENCE: 16

```
Met Pro Val Asp Leu Ser Lys Trp Ser Gly Pro Leu Ser Leu Gln Glu
1               5                   10                  15

Val Asp Glu Gln Pro Gln His Pro Leu His Val Thr Tyr Ala Gly Ala
            20                  25                  30

Ala Val Asp Glu Leu Gly Lys Val Leu Thr Pro Thr Gln Val Lys Asn
        35                  40                  45

Arg Pro Thr Ser Ile Ser Trp Asp Gly Leu Asp Ser Gly Lys Leu Tyr
    50                  55                  60

Thr Leu Val Leu Thr Asp Pro Asp Ala Pro Ser Arg Lys Asp Pro Lys
65                  70                  75                  80

Tyr Arg Glu Trp His His Phe Leu Val Val Asn Met Lys Gly Asn Asp
                85                  90                  95

Ile Ser Ser Gly Thr Val Leu Ser Asp Tyr Val Gly Ser Gly Pro Pro
            100                 105                 110

Lys Gly Thr Gly Leu His Arg Tyr Val Trp Leu Val Tyr Glu Gln Asp
        115                 120                 125

Arg Pro Leu Lys Cys Asp Glu Pro Ile Leu Ser Asn Arg Ser Gly Asp
    130                 135                 140
```

-continued

```
His Arg Gly Lys Phe Lys Val Ala Ser Phe Arg Lys Lys Tyr Glu Leu
145                 150                 155                 160

Arg Ala Pro Val Ala Gly Thr Cys Tyr Gln Ala Glu Trp Asp Asp Tyr
                165                 170                 175

Val Pro Lys Leu Tyr Glu Gln Leu Ser Gly Lys
            180                 185
```

FLORIGEN PATHWAY TOOLKIT

RELATED APPLICATIONS

This application is a national stage filing under 35 U.S.C. § 371 of International Patent Application Serial No. PCT/US2017/026635, filed Apr. 7, 2017, entitled "FLORIGEN PATHWAY TOOLKIT", which claims the benefit under 35 U.S.C. § 119(e) of U.S. Provisional Patent Application No. 62/321,178, filed Apr. 11, 2016, entitled "FLORIGEN PATHWAY TOOLKIT." The entire teachings of the referenced applications are incorporated herein by reference.

FEDERALLY SPONSORED RESEARCH OR DEVELOPMENT

This invention was made with government support under grant IOS-11237880 awarded by the National Science Foundation and grant 2016-67013-24452 awarded by the United States Department of Agriculture. The government has certain rights in the inventions.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Sep. 7, 2022, is named C130070030US02-SUBSEQ-DQB and is 10,486 bytes in size.

BACKGROUND

One of the most important determinants of crop productivity is plant architecture. For many crops, artificial selection for modified shoot architectures provided critical first steps towards improving yield, followed by innovations in agronomic practices that enabled large-scale field production. However, for many other crops, architecture was not targeted during domestication. A prominent example is tomato, in which the major driver of yield was a drastic increase in fruit size. Shoot architecture, in contrast, remained largely unchanged until the discovery, 85 years ago, of the self pruning (sp) mutation, which transformed 'indeterminate' plants into a radically new 'determinate' form. The ability to manipulate tomato architecture beyond sp in a simple and predictable way remains limited, which means that the potential of new shoot architectures to further improve yield and reduce production costs remains untapped.

SUMMARY

Described herein is a florigen pathway toolkit that comprises mutations in genes in the florigen pathway in Solanaceae, such as mutations in genes in the florigen pathway in tomatoes, that are useful to quantitatively modulate or adjust the balance of opposing flowering signals to customize and improve shoot architecture and flowering (flowering time) for tomato breeding, particularly for fresh market tomato breeding. Members of the toolkit include suppressor of sp (ssp) gene mutants, which are useful to restore indeterminate growth; Single Flower Truss (sft) gene mutants, which are useful to quantitatively manipulate determinacy to improve yield; sp gene mutants, the primary repressor of flowering and sympodial growth; and mutants of SP5G gene, an antagonist of florigen within the primary shoot. Members of the toolkit are chemically-induced alleles in genes that control the balance of opposing flowering signals; engineered alleles, such as CRISPR/Cas9 (CR-) engineered alleles, in such genes or a combination of these chemically-induced alleles and engineered alleles.

Described herein are heritable mutations in the SP5G gene in tomato plants, such as CRISPR/Cas9-induced heritable mutations in the SP5G gene, that alter flowering, shoot architecture and yield. Such heritable mutations have been shown to result in an "earliness" phenotype in tomato plants: tomato plants that are sp5g mutants, such as CR-sp5g mutants, flower earlier than corresponding WT tomato plants (corresponding tomato plants that do not comprise mutant sp5g/do not comprise mutant CR-sp5g). Flowering occurred earlier in sp5g mutants, such as in homozygous CR-sp5g mutants. However, the sympodial index (SI) or number of leaf nodes between successive inflorescences was not significantly different in sp5g mutant tomato plants and WT tomato plants. This earliness phenotype provided by sp5g mutations (e.g., by homozygous CR-sp5g mutants) can be valuable in breeding.

Also described here are early-yielding double-determinate sp5g sp double mutant plants (early-yielding double-determinate sp5g sp double mutant tomato plants) that result when sp5g mutations are combined with sp (when sp5g mutation is present in an sp mutant background). Sp5g mutations can be produced in any background (whether it is an sp mutant background or not); if it is not an sp background, CRISPR or other gene editing technology can be used to transform the determinate tomato plant into a double determinant by targeting both SP5G and SP and producing sp5g sp double mutants. Double determinate sp5g sp double mutant tomato plants are reduced in size, early-yielding and significantly more compact in size, compared, for example with corresponding sp (determinate) tomato plants. Double determinate tomato plants can be grown at higher density, for example, than is possible with other tomato plants, such as sp determinate plants. Further, at least in part because of the earliness effect, these tomato plants can be grown at higher latitudes, where the growing season is shorter; this is possible, in part, because of the earliness effect.

In one embodiment of an sp5g mutant, SP5G function has been eliminated; all or a portion of the SP5G gene has been deleted or altered and SP5G gene function (and that of the encoded protein) is eliminated. Mutations (deletions, alterations or both) can be made in any region or regions of the SP5G gene, such as in any portion of one or more of the exons (e.g., exon 1) or in a sequence that encodes a conserved SP5G sequence or a sequence that encodes a specific domain, such as the sequence encoding a conserved PEBP domain comprising amino acids 23-164 of SP5G protein (www.ncbi.nlm.nih.gov/Structure/cdd/wrpsb.cgi?INPUT_TYPE=live&SEQUENCE=AA 031793.1 and www.ncbi.nlm.nih.gov/Structure/cdd/cddsrv.cgi?uid=176644) or the sequence encoding the 14 amino acid external loop domain, to produce a null/loss of function sp5g mutant. NCBI Gene ID 101254900 (updated 15 Mar. 2016); ncbi.nlm.nih.gov/gene/101254900 and references cited. In an alternative embodiment, gene function and protein function are reduced. For example, the sp5g mutant results in production of functional protein at reduced levels (levels that result in the desired earliness phenotype).

SP5G gene function can be altered (eliminated or reduced) by any of a variety of types of mutations, as individual mutations or as a combination of mutations. Examples of different types of mutations include, but are not limited to, missense mutations, nonsense mutations, insertions, deletions, and duplications.

A missense mutation is a change in one DNA base pair of the SP5G gene; the codon that includes the change codes for a different (mutant) protein, and the substituted protein may be nonfunctional or may exhibit reduced activity (relative to a protein encoded by a non-mutated/wild-type SP5G gene). Thus, in some embodiments, the SP5G gene comprises a missense mutation that produces a gene encoding a nonfunctional protein. In some embodiments, the SP5G gene comprises a missense mutation that produces a gene encoding a functional protein that exhibits reduced activity relative to a protein encoded by the non-mutated/wild-type SP5G gene. In some embodiments, a missense mutation is in exon 1 of the SP5G gene.

A nonsense mutation or point mutation in the SP5G gene results in a premature stop codon or a nonsense codon in the transcribed mRNA; the encoded protein is truncated and typically is nonfunctional or exhibits reduced activity (relative to a protein encoded by a non-mutated/wild-type SP5G gene). In some embodiments, a mutant sp5g gene comprising a nonsense mutation encodes a truncated (shorter than full-length) nonfunctional protein. In some embodiments, a mutant sp5g gene comprising a nonsense mutation encodes a truncated (shorter than full-length) protein that exhibits reduced activity relative to a protein encoded by the non-mutated/wild-type SP5G gene. In some embodiments, a nonsense mutation or point mutation is in exon 1 of the SP5G gene.

An insertion changes the number of DNA bases in the SP5G gene by adding one or more (e.g., 1, 2 or 3) nucleotides. As a result, the protein encoded by a mutant sp5g gene may be nonfunctional or exhibit reduced activity relative to a protein encoded by the non-mutated/wild-type SP5G gene. In some embodiments, an insertion is in exon 1 of the SP5G gene. By contrast, a deletion changes the number of DNA bases in the SP5G gene by deleting one or more (e.g., 1, 2 or 3) nucleotides. As a result, the protein encoded by the mutant sp5g gene may be nonfunctional or exhibit reduced activity relative to a protein encoded by the non-mutated/wild-type SP5G gene. In some embodiments, a deletion is in exon 1 of the SP5G gene.

Insertions and/or deletions, collectively referred to as "indels," may result in a frameshift mutation, which changes the SP5G open reading frame. A frameshift mutation is caused, in some embodiments, by insertion or deletion of a number of nucleotides that is not divisible by three. In some embodiments, a frameshift mutation in the SP5G gene produces a gene encoding a nonfunctional protein. In some embodiments, a frameshift mutation in the SP5G gene produces a gene encoding a protein that exhibits reduced activity relative to a protein encoded by the non-mutated/wild-type SP5G gene.

In some embodiments, a mutation in a critical functional domain of the SP5G gene produces a gene that encodes a nonfunctional protein. For example, a mutation that alters a nonconserved amino acid in a critical functional domain of the SP5G gene may produce a gene encoding a nonfunctional protein.

In some embodiments, a mutation in a SP5G gene produces a gene that encodes a truncated protein. Preferably, truncation results in production of a nonfunctional protein. In some embodiments, truncation disrupts or alters a region of the SP5G protein critical to its function. Such a truncation can occur, for example, in the conserved domain comprising amino acids 23-164 of SP5G protein, the sequence encoding the 14 amino acid external loop domain or in both. Alternatively, truncation can occur at any location prior to amino acid 164 of SP5G protein. Truncation can result in production of a shortened version of SP5G protein, which has reduced function. Insertion results in addition of one or more base pairs to the SP5G gene and production of an altered protein. Deletion results in removal of one or more base pairs from the SP5G gene, such as a large deletion (a substantial portion or all of an exon, such as exon 1) that renders the gene nonfunctional. The resulting protein, as well, is out of frame and not produced or produced in an altered form, which is nonfunctional or has reduced function.

Particularly useful are null mutations. Such alterations in the SP5G gene mean that transcription into RNA does not occur, translation into a functional protein does not occur or neither occurs. A preferred embodiment is a null mutation of an exon, such as exon 1 of SP5G. One approach to creating null mutations is to target CRISPR-Cas9 mutagenesis to exons that encode functional protein domains. See, Shi, J. et al. (2015) Nature Biotechnology, 33(6): 661-667 and Online Methods.

The effects/advantages of sp5g mutants in breeding tomatoes can be assessed individually or in combination with other members of the florigen toolkit described herein, such as in combination with suppressor of sp (ssp) mutants, which are useful to modify determinate and indeterminate growth, including individual ssp mutants, individual sft mutants and combinations of ssp mutants and sft mutants, which are useful to quantitatively manipulate determinacy to improve yield; and mutants of sp, the primary repressor of flowering and sympodial growth. Assessment of the effects of sp5g mutants can be carried out individually (assessment of the effects of only an sp5g mutant) by focusing on evaluating earliness for yield in the standard Roma/plum background (M82). In addition, the easily genotyped CR-sp5g deletion allele can be introgressed into large-fruited inbred tomatoes and into small-fruited inbred tomatoes. The sp5g mutation can be generated by CRISPR in any genetic background, whether the plant (tomato plant) carries sp or not. In one embodiment, mutation in sp and mutation in SP5G can be generated in any indeterminate background, using CRISPR to target both sp and SP5G. Any indeterminate plant can be transformed into a double determinate plant by targeting both genes (sp and SP5G), thus removing the need for a time-consuming backcrossing/introgression program. Assessment of alleles and allelic combinations from the florigen pathway toolkit (e.g., any combinations of two, three or four of sp5g mutants, sft mutants, sp mutants and ssp mutants) will provide those that are useful and, in some embodiments, best, for fresh market tomato processing and processing tomato performance. For example, triple mutants (double-determinate sp5g sp and an additional, different mutation), such as sp5g sp sft-1906 and sp5 sp ssp-2129, can be produced to provide early-yielding tomato plants with enhanced yields. Quadruple mutants (double-determinate sp5g sp and two additional, different mutations), such as sp5g sp sft-1906 ssp-2129, can be produced, to provide early-yielding tomato plants with enhanced yields. Alternatively, the double mutant can be combined with heterozygosity for a mutation that would result in early and increased yield, such as combining sp5g sp with heterozygosity for sft-1906 mutation to produce sp5g sp sft-1906/+(double mutant plus heterozygosity for sft-1906 mutation). A further example of the double mutant combined with heterozygosity for a mutation from the florigen pathway toolkit is sp5g sp ssp2129/+.

As further shown, plants (tomato plants) comprising mutations in SP5G exhibit early flowering, compared to the corresponding plant (tomato plant) lacking the mutation in SP5G and grown under the same conditions as the sp5g mutant plants. Tomato plants comprising mutations in the first exon of SP5G showed early flowering of the primary shoot. Mutations can be created by a variety of known methods. For example, mutations can be created by the CRISPR/Cas9 method, using one or two guide RNAs that target a portion of SP5G gene. In one embodiment, mutation in the first exon of the SP5G gene is created by targeting the first exon by CRISPR/Cas9 using two guide RNAs (see, for example, FIG. 2 (a and b); gRNA, Target 1 and Target 2). CR-sp5g alleles a1 and a2 were identified from two independent first-generation (TO) transgenic plants. Representative plants comprising a mutant allele (e.g., CR-sp5g allele a1) show early flowering of the primary shoot. See FIG. 2c. CR-sp5g-a2 plants also show early flowering of the primary shoot, compared to the WT plant. In FIG. 2c, a red arrowhead marks an open primary inflorescence at anthesis in CR-sp5g-a1 plants after the sixth leaf (L6). WT plants have not yet flowered. (d, e) Primary shoot flowering time (FIG. 2d) and sympodial shoot flowering time (FIG. 1—SP5G-CRISPR e) from both primary and basal axillary shoots were compared in WT and CR-sp5g plants. As shown in FIG. 2d, the number of leaves to first inflorescence (an indicator of time) was significantly reduced in both primary shoots and basal axillary shoots in plants comprising SP5G with mutant first exon, compared to WT plants. As shown in FIG. 2e, the number of leaves per sympodial shoot in both primary and basal axillary shoots did not differ in sp5g mutants and WT plants. Mean values (±s.e.m.) were compared to WT using two-tailed, two-sampled t tests (*$p<0.05$, $p<0.01$, *$p<0.001$). ID: indeterminate. These results indicate that SP5G functions as a repressor of flowering and an antagonist of the flowering hormone florigen (encoded by SFT), but only within the primary shoot. SP, on the other hand, represses flowering and antagonizes florigen (SFT) activity during sympodial shoot cycling. Results show that mutations in SP5G alter flowering time in tomato, but not the SI.

As further shown here, early-yielding double determinate sp5g sp double mutant plants result when CR-sp5g mutations are combined with sp (e.g., classic sp breeding allele). See FIG. 3. Shown (a) are representative sp determinate (D) and CR-sp5g sp double determinate (DD) double mutant plants 80 days after they were transplanted to the field. Flowering time of primary (b) and sympodial shoots (c) in sp and CR-sp5g sp plants was compared and in both primary shoots and sympodial shoots, flowering time (as indicated by number of leaves to first inflorescence) was significantly earlier in CR-sp5g sp double determinate double mutant plants than in sp determinate plants. In addition, the CR-sp5g sp plants reach final harvest stage (90% red fruit) at least two weeks sooner than the sp determinate plants. (d) Important fruit quality traits include fruit weight and Brix (total soluble solids). Assessment of fruit weight and Brix showed that early yielding double determinate sp5g double mutant plants did not differ significantly from sp determinate plants in either characteristic. As shown, the overall shoots, whether from main or side shoots, flower earlier in the sp5g sp double mutants, causing the double determinate habit, still with high yields. The more compact plant will allow growth at higher latitudes where the growing season is shorter; this is possible, in part, because of the earliness effect. In addition, because the unexpected synergistic effect of combining sp5g and sp mutations together results in more compact plants that are still high yielding, the plants can be grown at higher density. For example, four sp5g sp double mutant tomato plants grown in the same square footage area as two sp single mutant tomato plants will produce a higher yield than the two sp single mutant plants.

Work described here has important implications in at least the following ways. First, results have shown that CRISPR/Cas9 can be used to create heritable mutations in florigen pathway family members that result in phenotypic effects. In the case of CR-sp5g mutants, the phenotypic effect is early flowering. Second, the different roles shown for SP5G and SP in primary and sympodial shoot flowering, respectively, suggest that homologous florigen antagonists have been selected to function in different shoot systems. The finding that sp5g mutants affect only flowering time of the primary shoot is surprising, as is the double mutant effect of more compact growth habit. Finally, the absence of phenotypic changes in CR-sp5g plants beyond flowering indicates potential for application. This can be evaluated, using known methods, such as in in elite germplasm. This can be done by integrating CR-sp5g mutations into an assessment of which alleles and allelic combinations from the florigen pathway toolkit are useful/best for fresh market tomato performance and processing tomato performance. This can be done, for example, by focusing on evaluating earliness in the standard Roma background (M82) and by introgression of the easily genotyped CR-sp5g deletion allele into large-fruited inbred tomatoes and small-fruited inbred tomatoes.

DETAILED DESCRIPTION

Figure 2:
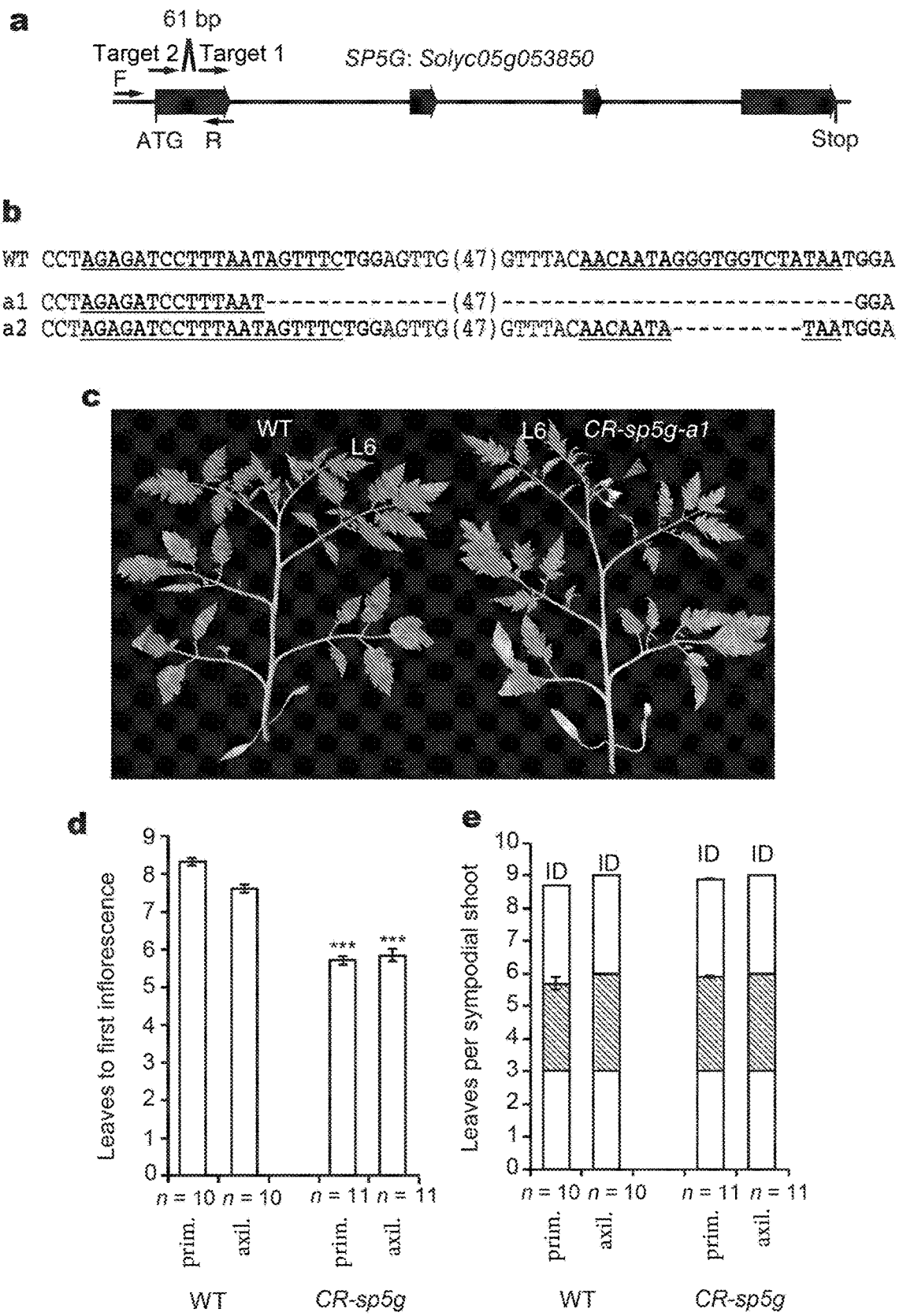
FIG. 2. CRISPR/Cas9-engineered mutations in SP5G result in early flowering. (a) The first exon of SP5G was targeted by CRISPR/Cas9 using two guide RNAs (gRNA, Target 1 and Target 2). (b) CR-sp5g alleles a1 and a2 identified from two independent first-generation (TO) transgenic plants. Note the insertion in a2, indicating a range of deletion and insertion alleles of various sizes can be. Sequences corresponding to SEQ ID NOs: 5-7 are shown, from Top to Bottom. (c) Representative plants of WT and CR-sp5g-a1 showing early flowering of the primary shoot. CR-sp5g-a2 plants are also early flowering. Red arrowhead marks an open primary inflorescence at anthesis in CR-sp5g-a1 plants after the sixth leaf (L6). WT plants have not yet flowered. (d, e) Primary shoot flowering time (d) and sympodial shoot flowering time (e) from both primary and basal axillary shoots in WT and CR-sp5g plants. Mean values (±s.e.m.) were compared to WT using two-tailed, two-sampled t tests (*$p<0.05$, $p<0.01$, *$p<0.001$). ID: indeterminate.
Figure 3:
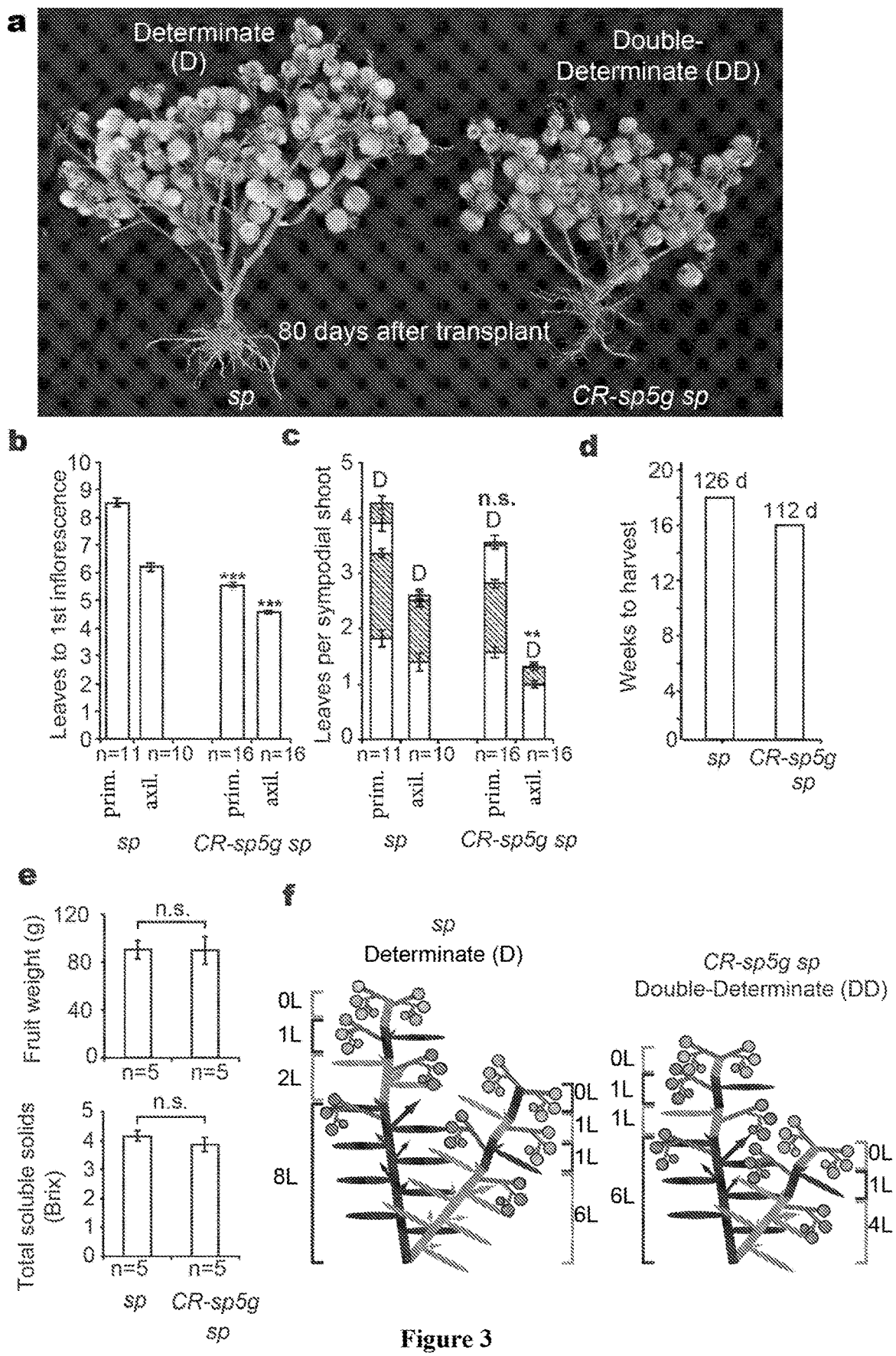
FIG. 3. Combining CR-sp5g mutations with sp results in early yielding double determinate sp5g sp double mutant plants. (a) Representative sp determinate (D) and CR-sp5g sp double-determinate (DD) double mutant plants 80 days after transplanting to the field. (b, c) Flowering time of primary (b) and sympodial shoots (c) in sp and CR-sp5g sp plants. Notably, flowering time is significantly earlier in primary, axillary, and sympodial shoots compared to sp and sp5g single mutants alone, or what would be expected from combining the additive effects of each mutation. (d) Number of weeks to final harvest (90% red fruits) in the sp and CR-sp5g sp genotypes. The CR-sp5g sp plants reach final harvest stage 2 weeks faster than sp plants. (e) Statistical comparisons of mean values for fruit weight (top) and total soluble solids (Brix) content (bottom) from sp and CR-sp5g sp plants showing fruit weight and brix are unaffected in CR-sp5g sp plants. Ten fruits were measured per replicate. Mean values (±s.e.m.) were compared to sp controls using two-tailed, two-sampled t tests (*p<0.05, p<0.01, *p<0.001). (f) Diagrams depicting shoot architectures of sp and CR-sp5g sp plants. Black bars and ovals represent shoot units and associated leaves. Alternating grey and black bars represent successive sympodial shoots. Arrows represent axillary shoots and green lines depict inflorescences. Colored circles represent maturing fruits. The number of leaves on primary, axillary, and sympodial shoots is indicated.

Described herein are induced mutations in the florigen pathway in plants, such as in Solanaceae, including tomato, that are useful to balance growth and termination to generate shoot architectures that result in increased yields of fruits (e.g., tomatoes) by modifying determinate growth. In specific embodiments, the mutations are in the SP5G gene and result in early flowering (e.g., FIG. 2). Combining sp5g mutations with sp results in early yielding double determinate sp5g sp double mutant plants (e.g., FIG. 3). The sp5g effects shown are in an sp mutant background (e.g., classic sp mutant background; e.g. M82), whether or not other mutant alleles (e.g. ssp, sft) are present in homozygous or heterozygous condition.

Several types of mutant alleles and allelic combinations, which comprise what is referred to herein as the florigen pathway toolkit, modify the opposing activities of SFT and SP to achieve better (e.g., enhanced or optimized) plant architectures for fresh market and processing field performance, such as in large-fruited and small-fruited tomatoes. Mutations in positive regulators of the florigen pathway in large-fruited and small-fruited elite plants create homozygous and heterozygous (hybrid) mutant genotypes with architectural modifications and yield improvements. Mutations can be made in any tomato plant in which the sp gene is mutated (in any plant in which there is sp background). For example, any of the many available tomato varieties in which sp is mutated can be used. Alternatively, any tomato variety or type in which sp can be mutated (e.g., an indeterminate tomato plant) such as through the use of CRISPR to target the sp gene, can be used. CRISPR technology can be used to target and alter both sp5g and sp genes in an indeterminate plant and produce a double determinate plant. Newly discovered alleles of sp, the primary repressor of flowering and sympodial shoot growth, are used to quantitatively modify determinacy and yield fresh market inbreds and hybrids. Dosage sensitivity of the florigen pathway has been shown and this has been used to modulate yield and plant architecture of Solanaceae and to produce gradients of yield and structure, ranging from classic mutant sp background through increasing strength of alleles (weak to stronger alleles), alone (single heterozygote) or in combinations (e.g., double or triple heterozygotes). Flowering time showed a gradient of delays that increased from single to double heterozygotes and with increasing allelic strength, due to combined dosage effects. All determinate phenotypes were higher yielding than sp plants. The florigen pathway toolkit includes chemically induced alleles and engineered alleles, such as CRISPR/Cas9 engineered alleles, useful for further fine-tuning of flowering signals, shoot architecture and yield. These tools are useful to quantitatively modify determinacy and yield of plants, such as tomatoes.

In specific embodiments, the mutant sspl gene and/or the mutant sft gene is present along with a mutant self-pruning (sp) gene in a double mutant background and the mutant sp gene (Pnueli et al. Development. 1998; 125(11):1979-89) comprises, for example, a coding sequence comprising a nucleic acid (e.g., DNA) having the sequence of SEQ ID NO: 8; a coding sequence comprising a portion of SEQ ID NO: 8 that exhibits substantially the same activity (e.g., encoding the same polypeptide or substantially the same polypeptide that has the same activity) as a nucleic acid (e.g., DNA) having the sequence of SEQ ID NO: 8; a coding sequence comprising a nucleic acid (e.g., DNA) having at least 85%, at least 90%, at least 95%, at least 96%, at least 97%, at least 98%, or at least 99% identity with the sequence of SEQ ID NO: 8; or a coding sequence comprising an orthologue or homologue of the nucleic acid having the sequence of SEQ ID NO: 8. In some embodiments, the mutant sp gene comprises a C to T mutation at position 227 of SEQ ID NO: 14.

SEQUENCES

SEQ ID NO: 8 is the nucleotide sequence of the coding sequence for wild-type tomato SP gene.
SEQ ID NO: 9 is the nucleotide sequence of the coding sequence of wild-type tomato SSP1.
SEQ ID NO: 10 is the nucleotide sequence of the coding sequence of ssp-2129, a mutant allele of SSP1.
SEQ ID NO: 11 is the nucleotide sequence of the coding sequence of ssp-610, a mutant allele of SSP1.
SEQ ID NO: 12 is the nucleic sequence of the coding sequence of wild-type SFT DNA.
SEQ ID NO: 13 is the nucleic sequence of the coding sequence of sft-1906, a mutant of SFT.
SEQ ID NO: 14 is the nucleotide sequence of the coding sequence of a mutant sp gene.
Nucleic Acid and Polypeptide Sequences >SP (Wild-Type) Coding Sequence ATGGCTTCCAAAATGTGTGAACCCCTTGTGAT-TGGTAGAGTGATTGGTGAAGTTGTT GATTAT-TTCTGTCCAAGTGTTAAGATGTCTGTTGTT-TATAACAACAACAAACATGTCT ATAATGGACATGAAT-TCTTTCCTTCCTCAGTAACTTCTAAACCTAGGGTT-GAAGTTCA TGGTGGTGATCTCAGATCCTTCTT-CACACTGATCATGATAGATCCAGATGTTCCTGGT CCTAGTGATCCATATCTCAGGGAACATCTACACTG-GATTGTCACAGACATTCCAGGC ACTACAGAT-TGCTCTTTTGGAAGAGAAGTGGTTGGGTAT-GAAATGCCAAGGCCAAA TATTGGAATCCACAGGTTTGTATTTTTGCTGTT-TAAGCAGAAGAAAAGGCAAACAAT ATCGAGTGCACCAGTGTCCAGAGATCAATT-TAGTAGTAGAAAATTTTCAGAAGAAA ATGAACTTGGCTCACCAGTTGCTGCTGTTTTCTT-CAATTGTCAGAGGGAAACTGCCG CTAGAAGGCGTTGA (SEQ ID NO: 8)

>SSP1 Coding Sequence

ATGTGGTCATCAAGCAGTGA-TAACAGGGGACTCTCTGCTTCTTCTTCTTCATCTT-CAT CCTCATCTCATTCACCATTTTCTCCAAGACT-

CAAAACAATGGAAGAAGTGTGGAAAG
ATATTAATCTTTCTTCACTTCAAGATCACAC-
TACGAATTACTCTAGAGATCATCATCA TCTTCAT-
GATCATAATCATCAAGCTGCTAATTTTGGTGGAAT-
GATTTTACAAGATTTT
TTGGCAAGGCCTTTTGCTAATGAATCTT-
CACCAGCAGCAGCAGCAGCAGCAGCCTCC
CCTGTTTCAGCTACAACTATGCTGAATTT-
GAACTCTGTTCCTGAGCTTCATTTCTTTG ATAACC-
CATTGAGGCAAAACTCAATCTTGCACCAAC-
CAAATGCAAGTGGAAGAAAA
AGGGTTGTCCCTGAAACAGAAGACAATTCTA-
CAGGGGATAGAAGAAATCAGAGGAT GAT-
CAAGAACAGAGAGTCTGCTGCTAGAT-
CAAGAGCTAGAAAGCAGGCTTATATGA
ACGAGTTGGAATCAGAAGTGGCACATTTAGTT-
GAAGAAAATGCAAGGCTCAAGAAG
CAGCAGCAACAGTTACGAGTAGATGCAGCTAAT-
CAAGTTCCCAAAAAGAACACTCT TTATCGGACGT-
CAACTGCTCCATTTGA (SEQ ID NO: 9)

>ssp-2129 Coding Sequence

ATGTGGTCATCAAGCAGTGA-
TAACAGGGGACTCTCTGCTTCTTCTTCTTCATCTT-
CAT CCTCATCTCATTCACCATTTTCTCCAAGACT-
CAAAACAATGGAAGAAGTGTGGAAAG
ATATTAATCTTTCTTCACTTCAAGATCACAC-
TACGAATTACTCTAGAGATCATCATCA TCTTCAT-
GATCATAATCATCAAGCTGCTAATTTTGGTGGAAT-
GATTTTACAAGATTTT
TTGGCAAGGCCTTTTGCTAATGAATCTT-
CACCAGCAGCAGCAGCAGCAGCAGCCTCC
CCTGTTTCAGCTACAACTATGCTGAATTT-
GAACTCTGTTCCTGAGCTTCATTTCTTTG ATAACC-
CATTGAGGCAAAACTCAATCTTGCACCAAC-
CAAATGCAAGTGGAAGAAAA
AGGGTTGTCCCTGAAACAGAAGACAATTCTA-
CAGGGGATAGAAGAAATCAGAGGAT GAT-
CAAGAACAGAGAGTCTGCTGCTAGAT-
CAAGAGCTAGAAAGCAGGCTTATATGA
ACGAGTTGGAATCAGAAGTGGCACATTTAGTT-
GAAGAAAATGCAAGGCTCAAGAAG
CAGCAGCAACAGTTACGAGTAGATGCAGCTAAT-
CAAGTTCCCAAAAAGAACACTCT TTATCGGACGT-
CAACTGCTCTATTTGA (SEQ ID NO: 10)

>ssp-610 Coding Sequence

ATGTGGTCATCAAGCAGTGA-
TAACAGGGGACTCTCTGCTTCTTCTTCTTCATCTT-
CAT CCTCATCTCATTCACCATTTTCTCCAAGACT-
CAAAACAATGGAAGAAGTGTGGAAAG
ATATTAATCTTTCTTCACTTCAAGATCACAC-
TACGAATTACTCTAGAGATCATCATCA TCTTCAT-
GATCATAATCATCAAGCTGCTAATTTTGGTGGAAT-
GATTTTACAAGATTTT
TTGGCAAGGCCTTTTGCTAATGAATCTT-
CACCAGCAGCAGCAGCAGCAGCAGCCTCC
CCTGTTTCAGCTACAACTATGCTGAATTT-
GAACTCTGTTCCTGAGCTTCATTTCTTTG ATAACC-
CATTGAGGCAAAACTCAATCTTGCACCAAC-
CAAATGCAAGTGGAAGAAAA
AGGGTTGTCCCTGAAACAGAAGACAATTCTA-
CAGGGGATAGAAGAAATCAGAGGAT GAT-
CAAGAACAGAGAGTCTGCTGCTAGAT-
CAAGAGCTAGAAAGCAGGCTTATATGA
ACGAGTTGGAATCAGAAGTGGCACATTTAGTT-
GAAGAAAATGCAAGGCTCAAGAAG
CAGCAGCAACAGTTACGAGTAGATGCAGCTAAT-
CAAGTTCCCAAAAAGAACACTCT TTATCGGACGT-
CAATTGCTCCATTTTGA (SEQ ID NO: 11)

>SFT (Wild-Type) Coding Sequence

ATGCCTAGAGAACGT-
GATCCTCTTGTTGTTGGTCGTGTGGTAGGGGATGT-
ATTGGAC CCTTTCACAAGAACTAT-
TGGCCTAAGAGTTATATATAGAGATAGAGAAGTTAA
TAAT GGATGCGAGCTTAGGCCTTCCCAAGTTAT-
TAACCAGCCAAGGGTTGAAGTTGGAGG
AGATGACCTACGTACCTTTTTCACTTTGGT-
TATGGTGGACCCTGATGCTCCAAGTCCG AGTGATC-
CAAATCTGAGAGAATACCTTCACTGGTTGGTCACC-
GATATTCCAGCTACC
ACAGGTTCAAGTTTTGGGCAAGAAATAGTGAGC-
TATGAAAGTCCAAGACCATCAAT GGGAATACATC-
GATTTGTATTTGTATTATTCAGACAATT-
AGGTCGGCAAACAGTGTA
TGCTCCAGGATGGCGTCAGAATTT-
CAACACAAGAGATTTTGCAGAACTTTATAATCT
TGGTTTACCTGTTGCTGCTGTCTATTTTAATTGT-
CAAAGAGAGAGTGGCAGTGGTGG ACGTAGAA-
GATCTGCTGATTGA (SEQ ID NO: 12)

>sft (Mutant) Coding Sequence

ATGCCTAGAGAACGT-
GATCCTCTTGTTGTTGGTCGTGTGGTAGGGGATGT-
ATTGGAC CCTTTCACAAGAACTAT-
TGGCCTAAGAGTTATATATAGAGATAGAGAAGTTAA
TAAT GGATGCGAGCTTAGGCCTTCCCAAGTTAT-
TAACCAGCCAAGGGTTGAAGTTGGAGG
AGATGACCTACGTACCTTTTTCACTTTGGT-
TATGGTGGACCCTGATGCTCCAAGTCCG AGTGATC-
CAAATCTGAGAGAATACCTTCACTGGTTGGTCACC-
GATATTCCAGCTACC
ACAGGTTCAAGTTTTGGGCAAGAAATAGTGAGC-
TATGAAAGTCCAAGACCATCAAT GGGAATACATC-
GATTTGTATTTGTATTATTCAGACAATT-
AGGTCGGCAAACAATGTA
TGCTCCAGGATGGCGTCAGAATTT-
CAACACAAGAGATTTTGCAGAACTTTATAATCT
TGGTTTACCTGTTGCTGCTGTCTATTTTAATTGT-
CAAAGAGAGAGTGGCAGTGGTGG ACGTAGAA-
GATCTGCTGATTGA (SEQ ID NO: 13)

>sp (Mutant) Coding Sequence

ATGGCTTCCAAAATGTGTGAACCCCTTGTGAT-
TGGTAGAGTGATTGGTGAAGTTGTT GATTAT-
TTCTGTCCAAGTGTTAAGATGTCTGTTGTT-
TATAACAACAACAAACATGTCT
ATAATGGACATGAAT-
TCTTTCCTTCCTCAGTAACTTCTAAACCTAGGGTT-
GAAGTTCA TGGTGGTGATCTCAGATCCTTCTT-
CACACTGATCATGATAGATCCAGATGTTCTTGGT
CCTAGTGATCCATATCTCAGGGAACATCTACACTG-
GATTGTCACAGACATTCCAGGC ACTACAGAT-
TGCTCTTTTGAAGAGAAGTGGTTGGGTAT-
GAAATGCCAAGGCCAAA
TATTGGAATCCACAGGTTTGTATTTTTGCTGTT-
TAAGCAGAAGAAAAGGCAAACAAT
ATCGAGTGCACCAGTGTCCAGAGATCAATT-

TAGTAGTAGAAAATTTTCAGAAGAAA
ATGAACTTGGCTCACCAGTTGCTGCTGTTTTCTT-
CAATTGTCAGAGGGAAACTGCCG
CTAGAAGGCGTTGA (SEQ ID NO: 14)

>sp5g Coding Sequence

CCATCTCATGTAATAAACAAAAATTGAGCTTAT-
TAATTATAATTGAGAAGAAAAAA AAT-
CATGCCTAGAGATCCTTTAATAGTTTCTG-
GAGTTGTTGGAGATGTTGTTGATCCA
TTCACAAGATGTGTAGACTTTGGTGTGGTTTA-
CAACAATAGGGTGGTCTATAATGGA TGTTCCTT-
GAGGCCTTCACAAGTTGTCAAT-
CAACCTAGGGTTGACATTGATGGAGAC
GATCTTCGTACTTTTTACACTCTGATTATGGTG-
GATCCTGATGCTCCAAACCCTAGCA ACCCAAACCT-
GAGGGAATATTTGCACTGGTTGGTCACAGA-
TATCCCAGCAGCCACA
GGAGCAACCTTTGGCAATGAAGTCGTGGGC-
TACGAGAGCCCACGACCCTCAATGGG AATC-
CATCGTTATATTTTCGTGTTGTATCGACAAT-
TGGGCTGCGATGCCATCGATGCA
CCGGACATAATCGATTCTAGACAAAATTT-
CAACACAAGAGACTTTGCTAGGTTTCAC
AATCTAGGTTTGCCTGTTGCTGCTGTTTACTTCAAT-
TGCAATAGGGAAGGTGGTACC GGTGGTCGTCGCC-
TATAAATCACCCCCCTCTCCTCGGGGTGC-
GATCCGTTCTCGAAC
TCTGTGTCAATGTCAGATGTTTTGTGTAACGGAT-
TTTTTGTTTGATAGTCACTCAGCT AAATTGCTTAT-
TAACTCAGAAAGTCATTTTTCTTTT-
TATCGAAGAAAATTGAAATTAT
GAGATAATAGCTATTATAGTTGAGTGATAATCT-
GAAAAAAAAAATCAACCATAATA TATATTATATAT-
TATATATATACCCAAAAAATAAAAGTCT (SEQ ID NO: 15)

>PEBP Protein Sequence

MPVDLSKWSGPLSLQEVDEQPQHPLHVTY-
AGAAVDELGKVLTPTQVKNRPTSISWDGL DSGK-
LYTLVLTDPDAPSRKDPKYREWHHFLVVNMKGN-
DISSGTVLSDYVGSGPPKGTG
LHRYVWLVYEQDRPLKCDEPILSNRSGDHRGKFK-
VASFRKKYELRAPVAGTCYQAEW DDYVPKLY-
EQLSGK (SEQ ID NO: 16)

Applicant's previous work has provided a general model for increasing tomato productivity in which enhanced yields can be achieved in the field by balancing flowering signals to shift the determinate growth of sp-classic toward indeterminate growth. Applicant has been successful in modifying antagonistic SFT/SP flowering signals to improve architecture and yield in a Roma cultivar and describes here modified forms of determinate growth that improve yields in both large-fruited and small-fruited fresh market breeding lines. See, PCT Application Publication Number WO 2014/081730 A1; Mutations in Solanaceae Plants That Modulate Shoot Architecture and Enhance Yield-Related Phenotypes and US Application Publication Number US 2014/0143898 A1, Mutations in Solanaceae Plants That Modulate Shoot Architecture and Enhance Yield-Related Phenotypes. Each of these cited applications is incorporated by reference herein in its entirety.

Components of the florigen pathway toolkit can be used in various combinations to create a range of shoot architectures in Solanaceae, particularly in tomato, such as fresh market tomatoes. For example, heterozygosity for ssp mutations can be used to manipulate the balance of flower promoting and repressing signals (SFT/SP ratios) in new ways and achieve improved architectures with higher yields. For example, ssp mutations and sft mutations are used to create a range of shoot architectures. sft mutant heterozygosity improves inflorescence (flower) production and yield as a result of dose-dependent suppression of sp. Activities of protein complexes are sensitive to changes in the dosage of their component parts, which can be adjusted accordingly to have a desired effect on inflorescence production, yield or both inflorescence production and yield. Heterozygosity for ssp mutations can be selected to influence/determine the balance of flower-promoting signals and repressing signals (expressed, in one form, as the SFT/SP ratio) in order to produce plants, such as tomato plants (e.g., fresh market tomato plants), with improved architecture and higher yield. Alternatively, heterozygosity for ssp mutations can be selected to reduce flowering, yield or both flowering and yield. A long-desired architecture for greenhouse tomato production—indeterminate varieties with two leaves between inflorescences (SI=2)—is produced using components of the florigen pathway toolkit. In one embodiment, ssp homozygotes in an sp background, such as ssp-2129 homozygotes in an sp background and ssp-610 homozygotes in an sp background, provide a genetic scheme to develop indeterminate varieties with two leaves between inflorescences (SI=2). Sympodial cycling in the sp background is sensitive to changes in florigen activity. Thus, the sft mutations and the ssp mutations can be used to modulate determinate growth quantitatively by means of allele-specific dosage effects. Further, because ssp and sft mutations affect different components of the same complex, individual dosage effects can be combined, making it possible to establish a set of genotypes that provide a gradient of sp suppression that results in highly desirable new architectural structures.

Exploiting dosage-sensitivity of the florigen pathway leads to a new optimum for processing tomato yield. When determinacy is gradually relieved, yields reach a new maximum before a further loss of flower-promoting signals results in a new balance that approaches wild type, resulting in a switch to indeterminate growth and progressively lower yields.

The florigen pathway toolkit is useful for improving architecture and yield in Solanaceae plants, such as tomato plants, including elite fresh market inbreds and hybrids. A variety of combinations of alleles, including homozygotes of each allele, single heterozygotes of each allele and double heterozygotes of two alleles, results in modified architecture, yield or both. Specific alleles that can be used include, but are not limited to, sft-1906, ssp-2129, ssp-610 and sft-tmf; resulting combinations include single homozygotes of each of sft-1906, ssp-2129, ssp-610 and sft-tmf; single heterozygotes of each of sft-1906, ssp-2129, ssp-610 and sft-tmf; and double heterozygotes of two alleles, viz., sft-1906/+ssp-2129/+; sft-1906/+ssp-610/+; sft-tmf/+ssp-2129/+; and sft-tmf/+ssp-610/+. Further mutant alleles that can be used are sft-4537 and sft-7187.

As described here, SP5G, which is a paralog of SFT in the Arabadopsis FT Glade, is similar to SP in that its external loop domain is divergent from SFT/FT, which suggests it has repressive flowering activity. Thus, SP5G likely encodes an antagonist of florigen function in parallel with SP. SP5G has effects on flowering time and forces early inflorescence production of the primary shoot, without affecting sympodial index/with little effect on leaf architecture. In tomato plants, sp5g mutant results in production of fewer leaves on the primary shoot; additional leaves do not have time to form before the shoot ends in inflorescence. In the wild type plant, earlier flowering caused by the sp5g mutation occurs without an effect on shoot architecture of the entire plant. In contrast, a homozygous double sp sp5g mutant tomato plant does not grow as tall because the primary shoot stops growing earlier than in wild type plants. The availability of sp5g mutants in the context of the sp mutant background provides a new toolkit component that can be used to modulate/fine tune additional characteristics—flowering time and compactness. For example, combinations with other mutants, such as sft and ssp1, may be useful in those situations in which sft and ssp1 mutations have an effect on flowering time, which can be compensated using sp5g.

Additional mutations, such as mutations in new regulators, including mutations outside the florigen pathway, are assessed to determine additive effects in combination with sft/+ or ssp/+ heterozygosity, providing even subtler fine-tuning of architecture and yield.

Use of the florigen pathway toolkit, alone or in combination with mutations outside the florigen pathway, results in a larger suite of novel germplasm for breeding higher yielding semi-determinate and indeterminate tomato varieties for both field and greenhouse production.

Described herein are induced mutations in the florigen pathway in Solanaceae, such as in tomato, that are useful to balance growth and termination to generate shoot architectures that result in increased yields of fruits (e.g., tomatoes) by modifying determinate growth. Several types of mutant alleles and allelic combinations from the florigen pathway toolkit described here can modify the opposing activities of SFT and SP to achieve better/optimized plant architectures for fresh market and field performance, such as in large- and small-fruited tomatoes. Mutations in positive regulators of the florigen pathway into large-fruited and small-fruited elite plants create homozygous and heterozygous (hybrid) mutant genotypes with architectural modifications and yield improvements. Newly discovered alleles of sp, the primary repressor of flowering and sympodial shoot growth, are used to quantitatively modify determinacy and yield in fresh market inbreds and hybrids. The toolkit includes chemically induced alleles and engineered alleles, such as CRISPR/Cas9 engineered alleles, which make possible further fine-tuning of flowing signals, shoot architecture, and yield.

Example CRISPR/Cas9-Induced Heritable Mutations in SP5G

Figure 1:
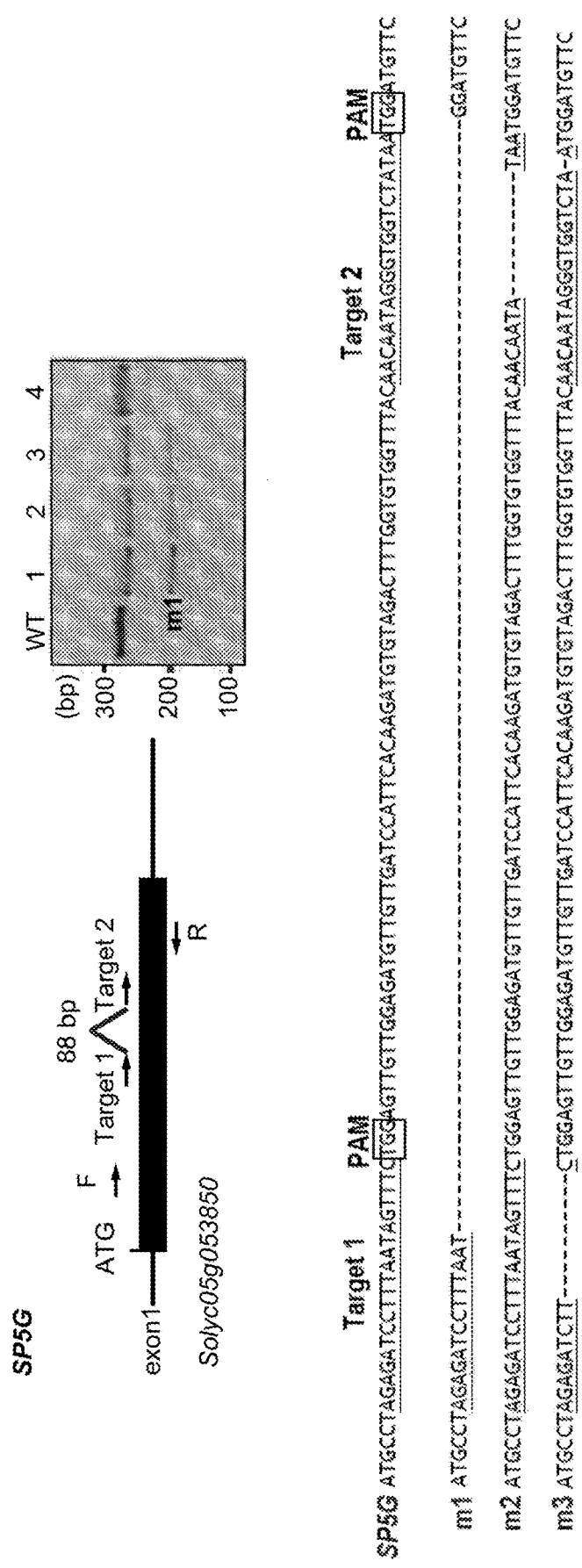
FIG. 1. CRISPR/Cas9 engineered mutations in SP5G. CRISPR/Cas9 targeting of SP5G, a CETS family homolog, showing sgRNAs for exon1, and generation of a desired large deletion in multiple TO chimeric plants. Sequences corresponding to SEQ ID NOs: 1-4 are shown, from Top to Bottom.

SP5G is the closest homolog of SFT (florigen), a tomato homologue of a key flower-promoting gene, FLOWERING LOCUS (FT). However, divergence between the functionally important external loop domain shared by SFT and SP5G suggests that SP5G may repress—not promote— flowering in tomatoes, in parallel with SELF PRUNING (SP) gene. Null alleles of SP5G were evaluated to assess their effects on flowering. In particular, CRISPR/Cas9-induced null alleles of SP5G were evaluated. For example, phenotypic changes caused by a large deletion detected by PCR in 3 out of 4 T0 CR-sp5g plants were assessed (FIG. 1). Initially, CR-spg5g T0 plants were outcrossed to wild type plants; heritability of the deletion allele was confirmed by PCR and sequencing. PCR was used to select plants lacking the Cas9 transgene, and as expected for a single hemizygous transgene insertion event in T0 plants, half of the F1 progeny were Cas9-free. Cas9-free F1 plants heterozygous for the large deletion were self-pollinated; and the phenotypes of resulting F2 progeny homozygous for the CR-sp5g deletion were evaluated (compared to wild type siblings). Homozygous CR-sp5g mutants flowered earlier than wild type siblings and quantification of this effect revealed that the primary inflorescence developed 2 leaves faster (sooner) in CR-sp5g mutants, resulting in an "earliness" phenotype. In contrast, the sympodial index of CR-sp5g plants was identical to that of wild-type plants. These results indicate that SP5G functions as a repressor of flowering and an antagonist of florigen (SFT), but only within the primary shoot. SP, on the other hand, is a repressor of flowering that acts only during sympodial shoot cycling.

What is claimed is:

1. An sp5g sp double mutant tomato plant comprising:
an sp5g mutant gene in an sp mutant background,
wherein the sp5g mutant gene comprises the coding sequence of SEQ ID NO: 15 having a null mutation in exon 1 (SEQ ID NO: 1),
wherein the sp mutant background is a tomato plant comprising a mutant sp gene comprising
(i) a sequence having at least 99% identity to SEQ ID NO: 8 or
(ii) a sequence comprising SEQ ID NO: 14,
wherein the sp5g sp double mutant tomato plant flowers earlier than a corresponding sp mutant tomato plant that does not comprise the sp5g mutant gene, as measured with reference to the number of leaves produced prior to appearance of first inflorescence.

2. The tomato plant of claim 1, wherein the mutation in exon 1 comprises a missense mutation, a nonsense mutation, an insertion, a deletion.

3. The tomato plant of claim 2, wherein the insertion produces an sp5g mutant gene comprising a frameshift or the deletion produces an sp5g mutant gene comprising a frameshift.

4. The tomato plant of claim 1, which is homozygous for the sp5g mutant gene.

5. The tomato plant of claim 4, wherein the tomato plant is homozygous for a clustered regularly interspaced short palindromic repeat (CRISPR) engineered sp5g mutant gene.

6. The tomato plant of claim 1, in which the sp5g sp double mutant tomato plant has a sympodial index that is the same as the sympodial index of the corresponding sp mutant tomato plant that does not comprise the sp5g mutant gene.

7. The tomato plant of claim 1, which is a Roma tomato plant, a large-fruited inbred tomato plant or a small-fruited inbred tomato plant.

8. A *Solanum lycopersicum* tomato plant homozygous for an sp5g mutant gene,
wherein the sp5g mutant gene comprises a null mutation in exon 1 (SEQ ID NO: 1),
wherein the tomato plant flowers earlier than a corresponding sibling *Solanum lycopersicum* tomato plant that does not comprise the sp5g mutant gene, as measured with reference to the number of leaves produced prior to appearance of the first inflorescence.

9. The *Solanum lycopersicum* tomato plant of claim 8, wherein the sp5g mutant gene is a CRISPR-induced heritable allele.

10. The *Solanum lycopersicum* tomato plant of claim 9, wherein the sp5g mutant gene is a CRISPR-induced heritable allele comprising a sequence having at least 99% identity to SEQ ID NO: 2, SEQ ID NO: 3, SEQ ID NO: 4, SEQ ID NO: 6 or SEQ ID NO: 7.

11. The *Solanum lycopersicum* tomato plant of claim 8, in which the tomato plant has a sympodial index that is the same as the sympodial index of a corresponding tomato plant that does not comprise the sp5g mutant gene.

12. The *Solanum lycopersicum* tomato plant of claim 8, which is a Roma tomato plant, a large-fruited inbred tomato plant, or a small-fruited inbred tomato plant.

13. A method of reducing time to production of first inflorescence in a tomato plant, as measured with reference to the number of leaves produced prior to appearance of the first inflorescence, comprising:
producing an sp5g sp double mutant tomato plant, an sp5g sp double mutant tomato seed or an sp5g sp double mutant tomato plant part that is homozygous for an sp5g mutant gene in an sp background and maintaining the sp5g sp double mutant tomato plant, the sp5g sp double mutant tomato seed or the sp5g sp double mutant tomato plant part under conditions under which the sp5g sp double mutant tomato plant, the sp5g sp double mutant tomato seed or the sp5g sp double mutant tomato plant part grows,
wherein the sp5g mutant gene comprises the coding sequence of SEQ ID NO: 15 having a null mutation in exon 1 (SEQ ID NO: 1),
wherein the sp mutant background is a tomato plant comprising a mutant sp gene comprising
(i) a sequence having at least 99% identity to SEQ ID NO: 8 or
(ii) a sequence comprising SEQ ID NO: 14.

14. The method of claim 13, wherein the sp5g mutant gene is a CRISPR-induced heritable allele.

15. The method of claim 13, wherein the sp5g mutant gene is a CRISPR-induced heritable allele comprising a sequence having at least 99% identity to comprising a sequence of SEQ ID NO: 2, SEQ ID NO: 3, SEQ ID NO: 4, SEQ ID NO: 6 or SEQ ID NO: 7.

16. The method of claim 13, in which the mutant tomato plant that is homozygous for the sp5g mutant gene has a sympodial index that is the same as the sympodial index of a corresponding tomato plant that is not homozygous for the sp5g mutant gene.

17. The method of claim 13, in which the mutant tomato plant homozygous for the sp5g mutant gene is a Roma tomato plant, a large-fruited inbred tomato plant or a small-fruited inbred tomato plant.

18. The *Solanum lycopersicum* tomato plant of claim 8, wherein the sp5g mutant gene encodes an SP5G protein comprising a mutation in the PEBP domain sequence of SEQ ID NO: 16.

19. The tomato plant of claim 1, further comprising a mutant suppressor of sp (ssp) gene; a mutant single flower truss (sft) gene; or a mutant suppressor of sp (ssp) gene and a mutant single flower truss (sft) gene,
wherein the mutant ssp gene comprises a mutation in an SSP gene comprising a coding sequence of SEQ ID NO: 9,
wherein the mutant sft gene comprises a mutation in an SFT gene comprising a coding sequence of SEQ ID NO: 13.

20. The tomato plant of claim 19, wherein the mutant ssp gene is heterozygous or the mutant sft gene is heterozygous.

21. The tomato plant of claim 1, wherein the sp5g mutant gene is a CRISPR engineered sp5g mutant gene.

22. The tomato plant of claim 5, wherein the CRISPR engineered sp5g mutant gene is CR-sp5g allele a1 comprising a sequence of SEQ ID NO: 6 or CR-sp5g allele a2 comprising a sequence of SEQ ID NO: 7.

23. The tomato plant of claim 19, wherein the mutant ssp gene is ssp-2129 comprising a sequence of SEQ ID NO: 10 or ssp-610 comprising a sequence of SEQ ID NO: 11.

24. An early-yielding double determinate tomato plant that comprises an sp5g mutant gene in an sp mutant background, wherein the double determinate tomato plant flowers earlier than the corresponding sp mutant tomato plant that does not comprise an sp5g mutant gene, as measured with reference to the number of leaves produced prior to appearance of first inflorescence, wherein the sp5g mutant gene comprises a mutation of SP5G in an exon that produces a null sp5g mutant; a mutation in a region of SP5G that encodes a conserved SP5G sequence that produces a null sp5g mutant; or a mutation in a region of SP5G that encodes a specific domain that produces a null sp5g mutant, wherein SP5G comprises the coding sequence of SEQ ID NO: 15, and wherein the sp mutant background is a tomato plant comprising a mutant (sp) gene comprising (i) a sequence having at least 99% identity to SEQ ID NO: 8 or (ii) a sequence comprising SEQ ID NO: 14.

25. The tomato plant of claim 19, wherein the mutant sft gene comprises a sequence of SEQ ID NO: 13.

* * * * *